United States Patent
Hillion et al.

(10) Patent No.: US 6,452,029 B1
(45) Date of Patent: Sep. 17, 2002

(54) PROCESS FOR THE CODIMERIZATION OF FATTY SUBSTANCE DIENES AND OLEFINS THAT ARE CATALYZED BY NICKEL COMPLEXES

(75) Inventors: Gérard Hillion, Herblay; Hélène Olivier, Rueil Malmaison, both of (FR); Katja Siepen, Erkrath (DE); Dominique Commereuc, Meudon; Robert Stern, Conflans Saint Honorine, both of (FR)

(73) Assignee: Institut Francais du Petrole, Rueil-Malmaison Cedax (FR)

( * ) Notice: Subject to any disclaimer, the term of this patent is extended or adjusted under 35 U.S.C. 154(b) by 0 days.

(21) Appl. No.: 09/362,217

(22) Filed: Jul. 28, 1999

(30) Foreign Application Priority Data

Jul. 28, 1998 (FR) .............................. 98 09671

(51) Int. Cl.$^7$ .............................. C09F 7/06; C09F 7/10
(52) U.S. Cl. .............................. 554/27; 554/25; 554/26; 554/29; 554/141; 554/223; 508/59
(58) Field of Search .......................... 554/26, 27, 141, 554/142, 223, 227, 29, 25; 562/546; 508/459

(56) References Cited

U.S. PATENT DOCUMENTS 5,434,282 A * 7/1995 Stern et al. .................. 554/227

FOREIGN PATENT DOCUMENTS

| EP | 0231748 | * 8/1987 | ............. C07C/2/36 |
| WO | 91/11428 | 8/1991 | |

OTHER PUBLICATIONS

Pillai et al, Codimerization of 2,5–norbornadiene with ethylene using soluble cobalt and nickel catalysts, AN 1994:8995 CAPLUS abs and citation, 1994.*

* cited by examiner

Primary Examiner—Deborah D. Carr
(74) Attorney, Agent, or Firm—Millen, White, Zelano & Branigan, P.C.

(57) ABSTRACT

A nickel catalytic system that makes it possible to obtain branched compounds from fatty substances by reacting simple olefins on polyunsaturated esters, which may or may not be conjugated, is described. The compounds that are obtained may be hydrogenated and used as lubricant bases or may be transformed according to known procedures into compounds of acid, alcohol, amine or amide type, used in varied applications.

39 Claims, 2 Drawing Sheets

PROCESS FOR THE CODIMERIZATION OF FATTY SUBSTANCE DIENES AND OLEFINS THAT ARE CATALYZED BY NICKEL COMPLEXES

FIELD OF THE INVENTION

The invention has as its object a new process for obtaining chemical compounds that are derived from polyunsaturated fatty substances, whereby said compounds are characterized by the presence, along the linear hydrocarbon-containing chain, of one or more branches of at least two carbon atoms.

These compounds are obtained by adding olefins to polyunsaturated fatty substances in the presence of a nickel catalytic system.

These unsaturated codimers can be hydrogenated, and saturated fatty substances that are characterized by a melting point that is generally below −20° C., significant thermostability, and desired surfactant properties are then obtained.

BACKGROUND OF THE INVENTION

The presence of branches in the compounds with a fatty substance base, mainly when these branches are located toward the center of the linear chains that comprise 14 to 18 carbon atoms, is reflected by a certain number of remarkable properties, such as, for example:

the very significant lowering of melting points, pour points and cloud points and an appreciable increase of the viscosity of the branched fatty substances relative to the same unbranched linear compounds; this property is used, for example, in lubricants, fats or plasticizers, where esters of fatty substances, salts or branched alcohol esters, whose acid can be organic or mineral, are used;

the reduction of the surface tension and the interfacial tension, whereby these characteristics are still studied in the field of surfactants and emulsifiers; this reduction makes it possible to obtain lower CMC (Critical Micellar Concentration);

the inhibition of the crystallization of branched soaps that may or may not be mixed with standard soaps, which makes it possible to obtain transparent soaps;

an increase of hydrophilicity, which makes the branched compounds more soluble or more wettable; a possible use would be to use quaternary salts of branched fatty acids in the emollients where softening is on an equal footing with a certain wettability;

a modification of the surface of the molecule, surface characterized by gaps that are created by the presence of branches; the cosmetic application of this property makes it possible to consider skin cream formulas which allow water vapor to pass, for example bases that consist of branched acid esters or even esters where the acid and the alcohol are both branched;

increased solubility of heavy metal salts with branched acids, which makes them soluble either in water or in certain organic solvents; the applications are multiple such as drying agents in paints, such as pigments, in the extraction of metals or anticorrosion, where it is possible to use calcium salts, alcanolamine salts or even amine salts as active agents. The branched acid salts also offer a greater compatibility of certain mineral feedstocks with polymers, which makes it possible to increase the feedstock ratio in plastics;

the bactericidal or bacteriostat effect that is more or less pronounced according to the nature of the bacteria and the number or magnitude of branches makes it possible to protect creams against bacterial attack or to replace quaternary salts in formulations that may or may not be basic; another use exists as an inhibitor of the evaporation of water, where, for example, compounds such as a branched alcohol or a branched acid monoglyceride make it possible to delay biodegradability and therefore to save the inhibitor.

The reaction of olefins with butadiene or other dienes has been known for a long time and was the object of several reviews. The codimerization of butadiene with ethylene leads to hexadiene-1,4; codimerization of ethylene with isoprene leads to methyl-3 hexadiene; and, finally, by codimerization of ethylene with piperylene, vinyl-2-pentane is obtained. Many catalysts are used to carry out these reactions. It is possible to cite, for example, rhodium, ruthenium, palladium, cobalt, iron, or nickel systems. Systems with a titanium base have been described (Connel, Laurence G.-Ann. N.Y. Acad. Sci. (73), 214, 143–9) to catalyze the formation of vinylcyclobutane from ethylene and butadiene.

In contrast, the addition of olefin to functional dienes has rarely been described. U.S. Pat. No. 3,742,080 points out the possibility of adding ethylene to dienes, of which one or two ends of the hydrocarbon-containing chains are substituted by halogen or alkoxy groups.

It is also known that an olefin can react on a conjugated diene or triene compound according to a Diels-Alder-type reaction. For example, the addition of ethylene to polyunsaturated fatty substances by simple heating to a temperature of 290° C. is described (R. E. Beal et Coll. JAOCS 52, 400 (1975)). Thus, a compound that has an unsaturated cycle with 6 carbon atoms in its hydrocarbon-containing chain is obtained from methyl linoleate and ethylene. After hydrogenation, these compounds have advantageous properties. Their melting point, however, which is above 10° C., is still too high to allow them to be used as lubricants.

Another method for obtaining branched compounds of fatty substances is known. It consists in reacting, according to a Wittig-type reaction, a ketone, such as, for example, the methyl ester of 12-oxo octadecanoic acid with an ylide, for example, the link $P(\emptyset)_3$=$CHCH_3$, where $\emptyset$ represents a phenyl radical. The compound $CH_3(CH_2)_5C$(=$CHCH_3$) $(CH_2)_{10}COOCH_3$, which can be hydrogenated into methyl ethyl-12-octadecanoate, is then obtained (D. G. Chasin et Coll, Chem. Phys., Lipids (71) 6, 8–30).

In nature, the presence of branched saturated compounds of fatty substances that are found in Koch bacteria, for example, or, with another length of hydrocarbon-containing chain, in mutton fat has also been pointed out.

Finally, it is known that the products that are referred to as "isostearic" contain traces of compounds that carry ethyl- or vinyl-type branches.

Recently, international patent applications WO-A-91/11428, 91-11427, 91/11426, and 91/11425 described obtaining branched fatty substance compounds by a catalytic process. The addition of olefin, such as ethylene or propylene, to the polyunsaturated fatty substance, a linoleic acid ester, for example, is catalyzed by a system with a base of rhodium, iridium, palladium, or ruthenium. The systems with rhodium, which are the only ones to have been described in an obvious way, are not very active, however.

U.S. Pat. Nos. 5,476,956 and 5,434,282 describe the use of a very specific rhodium catalytic system that makes it possible to accelerate the addition of olefin to the fatty substance dienes, particularly conjugated dienes, by a factor of 50 to 100. This process, however, is still very difficult to apply on a large scale due to excessive rhodium consumption.

Published French Patent Application FR-A-2 766 482, in the name of the same applicant, describes a process that uses a cobalt catalytic system, which consists in reacting simple olefins, for example ethylene, on polyunsaturated esters, for example the methyl linoleate that may or may not be conjugated, to obtain branched esters. The branched compounds that are obtained can be hydrogenated and used, among other things, as lubricant bases. This patent application describes a process for obtaining a codimer in which co-catalysts can optionally be introduced, such as, for example, transition metals such as iron, nickel, copper, rhodium or palladium. These catalysts make it possible to catalyze the conjugation, if a start is made from an unconjugated polyenic ester, and therefore to accelerate the reaction.

SUMMARY OF THE INVENTION

It has now been found, surprisingly enough, that by using a simple nickel compound with an acid reducing agent or a reduced nickel compound with a Bronsted or Lewis acid, it was possible, in the presence of a ligand, to obtain the main reaction of ethylene addition or another olefin to the ester, which may or may not be conjugated, under particularly mild conditions, since it is possible to obtain total conversion of conjugated esters with less than 0.1 MPa of ethylene pressure and between 30 and 80° C. In addition, thanks to the increased reactivity of these nickel catalysts, it is possible to obtain the addition of 2 or 3 ethylene radicals on the diene substrate.

Whereby nickel is highly conjugating, it is possible in one stage also to obtain an addition product by starting from a polyenic ester that is not conjugated but can be conjugated.

DETAILED DESCRIPTION OF THE INVENTION

The object of this invention is therefore a new process for codimerization of a monoolefinic compound with a polyunsaturated fatty substance in the presence of a catalytic system that comprises a nickel compound. Owing to this type of catalyst, it is possible to envision significantly reducing the cost of this reaction and to obtain improved selectivity relative to the products that are obtained with the rhodium complexes and an increased reactivity relative to cobalt complexes and, consequently, on the one hand, to work easily at atmospheric pressure and, on the other hand, to obtain easily heavier compounds with the addition of 2 or 3 ethylene radicals in the polyenic compounds.

The so-called "polyunsaturated or polyenic fatty substance" compound that is employed in the reaction on which the process of the invention is based is generally a compound that comprises, on the one hand, at least two ethylene bonds, whereby these bonds can be conjugated or are able to be conjugated two by two, and, on the other hand, a carboxylic group such as the one that is present in fatty acids that have 18 to 26 carbon atoms. Sunflowerseed, safflower, fish, linseed, soybean, oiticica, cottonseed, colza, Chinese wood, nut, corn, linola, and grape seed oils and generally all the oils or their derived esters that comprise polyunsaturated compounds are conceivable as raw materials.

The fatty acids that are being considered, whether they be dienes, trienes, or polyenes, are used in the form of their esters that are formed either from fatty acids or oils by reaction with monofunctional alcohols, such as, for example, methanol, ethanol, 2-ethylhexanol or isopropanol; difunctional alcohols, such as, for example, neopentylglycol; trifunctional alcohols, such as, for example, trimethylolpropane; and polyfunctional alcohols, such as, for example, sorbitol, polyglycerols, pentaerythritol and sugars. The oils themselves, as glycerol esters, are possible substrates.

These esters can initially be conjugated partially or totally or be unconjugated. In other words, they can contain at least two double ethylene bonds that may or may not be separated by a methylene group. Among the best-known processes for conjugating double bonds, it is possible to cite those that use alkaline alcoholates in the presence or absence of a solvent. It is possible in this case to obtain up to 99% of fatty substance that is conjugated relative to the polyunsaturated fatty substance that is initially present in the oil.

Other conjugating catalytic systems that employ ruthenium or carbonyl iron complexes are known. The nickel system is itself conjugating and can be used during or before the reaction with ethylene.

The monoolefinic compound that is employed in the reaction may consist of any reactive olefin that is selected from among the ordinary monoolefins (monoolefinic hydrocarbons), such as, for example, ethylene, propylene, or butene-1, and preferably ethylene.

The process for preparing branched fatty substances is characterized in that at least one monoolefinic compound is added to a fatty substance that comprises at least two ethylene bonds that may or may not be conjugated in the presence of a catalytic system that comprises at least one nickel compound, at least one reducing compound and/or at least one Bronsted or Lewis acid and at least one ligand.

The nickel compound may be a bivalent and in this particular instance monovalent or zerovalent inorganic or organic nickel salt. Among the bivalent nickel compounds, it is possible to cite halides, thiocyanates, sulfates, nitrates, alcoholates, carbonates, carboxylates, beta diketonates or beta acetocarboxylic acid esters; special examples of usable nickel salts are nickel (II) chloride, bisacetylacetonatonickel (II), and nickel (II) acetate. Among the zerovalent compounds, it is possible to cite nickel bis-cyclooctadiene [(Ni(COD)$_2$], but also Raney nickel.

As reducing compounds, it is possible to cite as examples the organoaluminum compounds of general formula $R_xAlX_{3-x}$ or $R_4Al_2SO_4$, where R is hydrogen or an alkyl group, where x=1, 2 or 3, and/or X is a halogen; the organomagnesium compounds of formula RMgX, with R=alkyl or aryl and X=halogen; and aluminoxanes. Preferably, fairly strong acid compounds will be used, such as dichloroethyl aluminum, dichloroisobutyl aluminum, or in general reducing agents such as $AlX_2R$ with R=alkyl; but these compounds can also be formed in situ from nickel chloride and dialkylchloroaluminum, or in the presence of aluminum chloride and alkylaluminum. If the nickel compound is zerovalent, it is possible to add a Lewis acid, such as $HPF_6$, $HAlCl_4$, $HBF_4$ or HCl.

The ligand may be selected:
  from among the phosphorus compounds of formula $PR_mX_{3-m}$ with m=2 or 3; R=aryl or alkyl; X=halogen; phosphites of formula $P(OR)_3$, with R=aryl or alkyl; phosphine oxides of formula $POR_3$; and diphosphines of formula $R_2P-(CH_2)_n-PR_2$, with R=aryl or alkyl, and n=0–4;
  from among the analogue compounds of arsenic or antimony, and
  from among the nitrogenous ligands, such as, for example, the amide derivatives, the imines or diimines (produced by, for example, reaction of glyoxal with a derivative of the aniline that is substituted on the aromatic core), and finally the pyridine derivatives, such as, for example, dipyridyl.

It is optionally possible to employ an organic compound that plays the role of a solvent; as solvents, it is possible to use aliphatic or aromatic hydrocarbons, ethers, esters, and halogenated hydrocarbons. The reaction can also be carried out preferably in the absence of solvent. This is then the ester of which a portion does not react with the olefin that acts as solvent; this is the case in particular with saturated esters or monoolefinic esters.

The molar ratio between the ligand and the nickel compound is preferably between 0.5/1 and 30/1, in particular between 1/1 and 4/1.

If the ligand coordinates for a coordination site, it is advantageous to use it with a ligand/nickel molar ratio that is between 1/1 and 4/1. If the ligand is bicoordinating, it is used with a molar ratio of between 0.5/1 and 2/1.

The molar ratio between the reducing agent and the nickel compound is generally between 1/1 and 30/1, and preferably between 4/1 and 15/1. If this is a Lewis acid that is added to the nickel that is already reduced, the ratio of reducing agent to nickel can be in this case from 1/1 to 3/1.

Generally, the nickel complex that comprises the ligand is dissolved in the diene ester and, under ethylene atmosphere, the reducing agent is introduced. If it is desired to work under ethylene pressure, the same operating procedure is followed by introducing ethylene pressure into the equipment only after the reducing agent has been added.

The catalytic composition is added to the system in a catalytic quantity. This quantity is expressed as being $10^{-3}$ to $10^{-1}$ mol of nickel per mol of unsaturated fatty substance, which may or may not be conjugated, and preferably $10^{-2}$ to $10^{-3}$ mol of nickel per mol of diene. The reaction temperature is in general 30 to 120° C. and preferably 50 to 80° C. The pressure of ethylene or propylene is 0.1 to 30 MPa, preferably 0.1 to 0.5 MPa. The time depends on the concentration and the nature of the catalyst. The time can be short, for example from several minutes to several hours. It is preferable to cut off the intake of ethylene when the diene has been consumed to avoid the dimerization of the ethylene.

It is possible to operate according to a continuous or intermittent process. The introduction of the catalyst and esters into the reactor can be done in the presence of ethylene at low temperature or at higher temperature directly into the reactor.

It is possible to operate with a supported, insoluble catalyst, for example, by attaching the nickel to a polymeric, heterogeneous phosphinic substrate, but also by using a Raney nickel with ligands.

The branched fatty substances that are obtained can be hydrogenated to obtain more stable products. The hydrogenation of the olefinic compounds has been known for close to 30 years. It was carried out particularly in 1971 by Chasin, cited above. The catalysts that can be used are those that are known for hydrogenating olefins, namely Raney nickel, palladium on carbon, supported nickel, generally after the codimerization catalyst has been eliminated by washing with water. It is sometimes possible to use the codimerization catalyst as a hydrogenation catalyst. After hydrogenation, the unbranched saturated compounds are eliminated by crystallization or by distillation. It is also possible to distill before hydrogenation to concentrate the branched products. This distillation will be done all the more easily as two ethylene molecules will have been attached to the substrate, which will make it possible to separate easily an ester with 22 carbon atoms from an ester with 18 carbon atoms on the lipidic chain. These esters with 18 carbon atoms and secondarily with 16 carbon atoms which are part of the initial substrate and which cannot react are saturated or monoolefinic esters, such as, for example, esters of palmitic, stearic or oleic acid. This is often the case if a start is made from a polyolefinic vegetable oil, such as, for example, sunflowerseed oil, which may or may not be transesterified.

The branched esters can be used as lubricant or emulsifying bases, or to undergo other treatments, such as transesterification with heavier alcohols when methyl esters are involved initially.

Finally, they can react like ordinary esters by being subjected to hydrogenolysis or transformation into amines or amides.

The entire disclosure of all applications, patents and publications, cited above and below, and of corresponding French application 98/09671, filed Jul. 28, 1998, are hereby incorporated by reference.

The following examples illustrate the invention; they are not limiting.

EXAMPLE 1

The reagents are as follows:

a) 5.5 g of a $NiCl_2(PBu_3)_2$ complex that is produced by reaction of hydrated nickel chloride and tributylphosphine according to a known procedure.

With the molecular weight being 534, the quantity of 5.5 g corresponds to 10.3 mmol of nickel, or on the order of 650 ppm (parts per million) relative to the weight of methyl ester that is used.

b) 1000 ml of methyl ester of previously conjugated sunflowerseed oil (EMTC); this volume corresponds to 870 g of ester that contains on the order of 65% conjugated methyl linoleate, present in 9 cis-11 trans and 10 trans-12 cis form.

This ester can be produced from a methyl ester of sunflowerseed oil by action of a potassium alcoholate at 120–130° C. The reaction product is washed, dried and distilled. An ester whose acid index (A.I.) is less than 0.6, which corresponds to 1 mmol of oleic acidity/100 g, is obtained.

If the necessary precautions to reduce the acidity of this conjugated ester are not taken, there is a larger consumption of reducing agent.

c) 14 ml or 96.6 mmol (d=1.26 to 30° C.) of ethylaluminum dichloride (EADC). The ratio between the reducing agent and the nickel complex is 9:1 by mol. The use of this reagent imposes the precautions of use for the sampling via a perfectly dry syringe.

d) Ethylene is available under pressure in a ballast of known volume. To follow the consumption with precision, it is necessary to heat the ballast above the critical point of the gas.

Experimental Part

Figure 1:
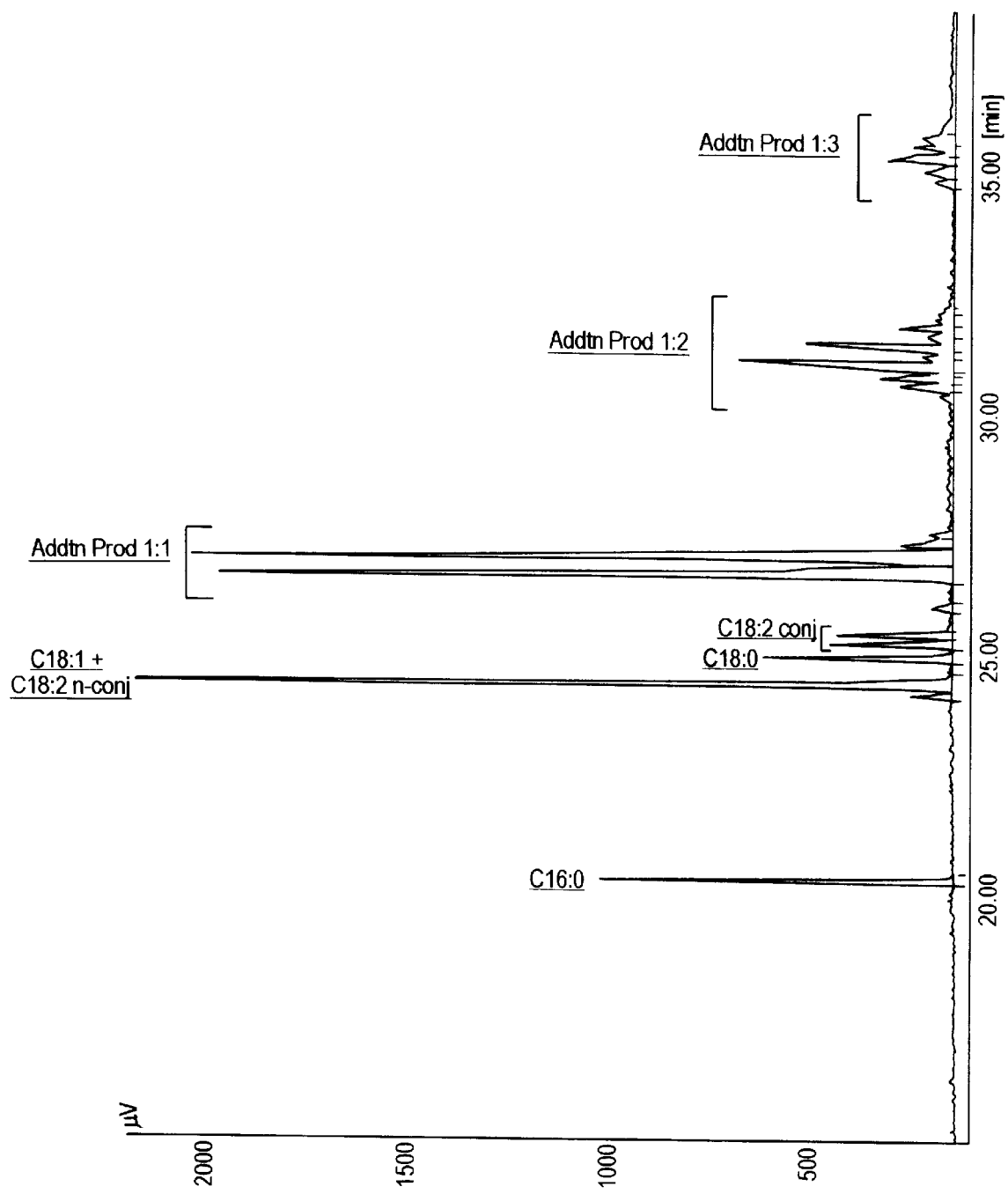
FIGS. 1 and 2 are gel permeation chromatogram sheets as described hereinafter.
Figure 2:
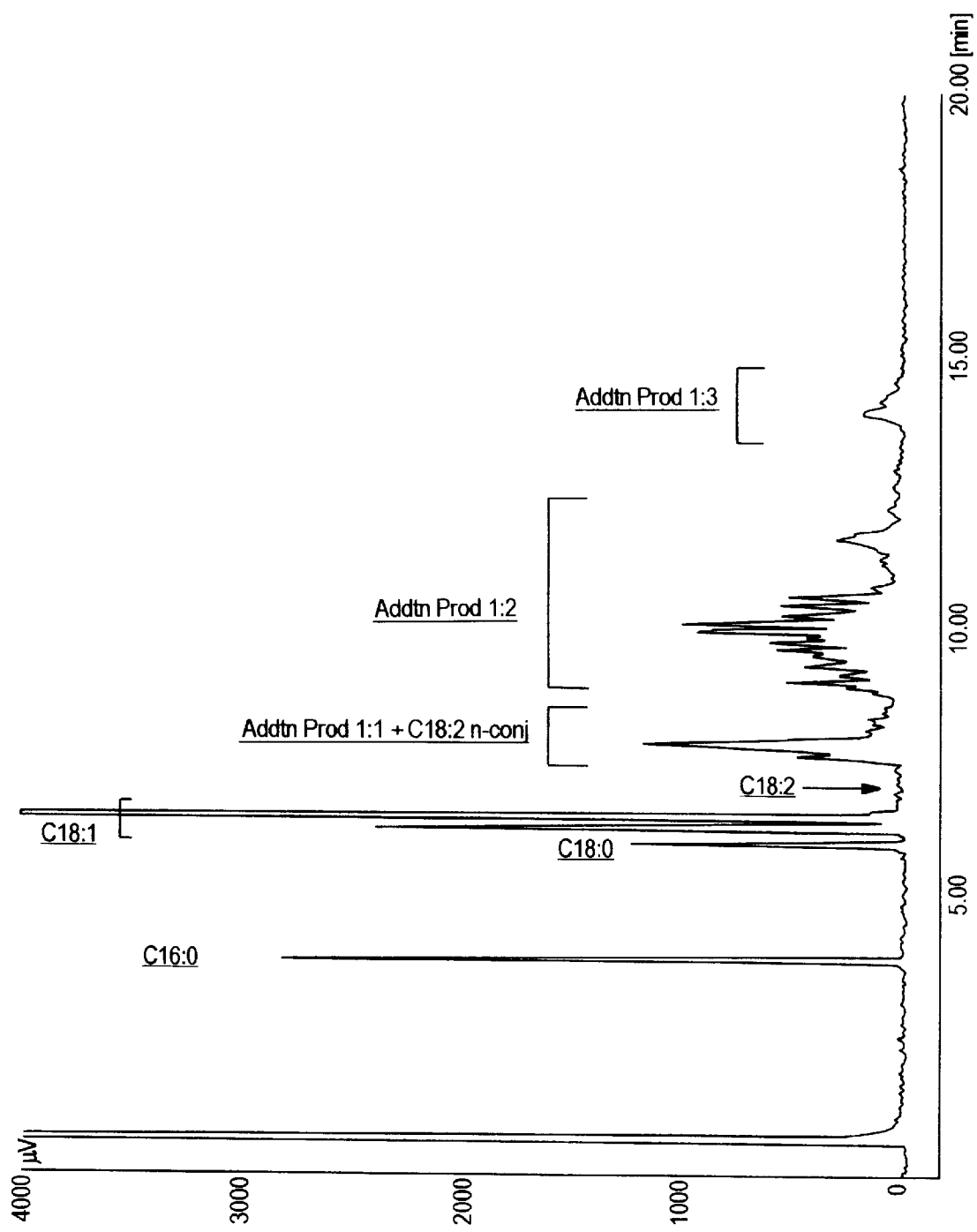

After the chamber is dried and made inert, the entire conjugated ester and the nickel complex that are stirred via a turbine until completely dissolved are introduced into a glass 3-liter reactor with a double jacket, heated by a thermal fluid. A red solution is then obtained. This mixture is heated to 80° C., and the ethylene solution is saturated by a controlled bubbling. With the equipment being provided with a septum, the quantity of reducing agent (EADC) is introduced with a syringe at one time.

Throughout the reaction, the stirring as well as the ethylene bubbling are maintained. As soon as there is no longer ethylene consumption, the catalytic activity is neutralized by adding water and methanol.

Sampling is carried out every hour when, for a drawn-off volume of 2 ml of solution, the sample is treated with 2 ml of methanol, 1 ml of water and 3 ml of n-heptane to destroy excess reducing agent. The upper organic phase is analyzed by gas phase chromatography.

Analysis by CPG [GPC] (Gel Permeation Chromatography)

Maximum information is obtained by using two suitable columns.

The first is a 50 mm capillary column of PONA type that makes it possible to analyze the compounds that are obtained by adding one, two or three ethylenes that are added to the diene ester. The families of products with 18, 20, 22 and 24 carbon atoms are separated easily, but in contrast, the separation between C18:1 (oleic) and C18:2, unconjugated (linoleic) (sheet 1/2), is not obtained.

The second is a 50 m capillary column that is called BPX70 (very polar phase), which separates all the isomers of esters of C18, but to the detriment of addition compounds, which are very poorly differentiated. A sample chromatogram is provided, attached (sheet 2/2).

Purification of the Reaction Product and Methods that are Used to Isolate the Addition Products At the end of the reaction, the ester solution is black. This solution is treated with methanol, then with water to destroy all of the reducing agent (EADC: ethyl aluminum dichloride). During this treatment, a significant release of gas occurs, and the color of the solution changes from brown to yellow with the formation of considerable white aluminum hydroxide precipitate. The separation of the ester phase that is thus freed of catalyst is facilitated by the addition of n-heptane.

After the solvent has evaporated, the ester phase is distilled under reduced pressure. A top fraction that represents about 5% by volume of the product that is to be distilled is eliminated. In this fraction, a portion of the ligand (tributyl phosphine) and a mixture of methyl esters that comprise C16 and C18 chains are recovered. The second fraction that is recovered has been distilled under a dynamic vacuum on the order of 2 mm of mercury and at a temperature of between 170 and 210° C.

The distillation residue represents about 5% by volume of the initial product.

The distilled product is introduced into a 1 liter autoclave to hydrogenate all of the double bonds with a nickel catalyst (catalyst that is generally used for the hydrogenation of vegetable oils). The hydrogenation is carried out at 200–210° C. under 3 MPa of hydrogen. After 5 hours of reaction, hydrogen is no longer consumed.

To isolate the branched esters, the unbranched saturated esters that are mainly methyl palmitate and methyl stearate are eliminated by fractional crystallization in acetone. The methyl palmitate is the most difficult impurity to eliminate. A liquid product that contains about 95% of addition products is thus obtained. The crystallization yield is very good. After washing with cold acetone, the crystallized solid product contains less than 0.5% of addition products.

| Methyl Esters of Fatty Acids | Before Hydrogenation | After Hydrogenation |
|---|---|---|
| C16:0 (palmitic acid) | 6.10 | 5.90 |
| C18:0 (stearic acid) | 3.90 | 33.10 |
| C18:1 (oleic acid) | 28.80 | 0 |
| C18:2 (linoleic acid) | 0 | 0 |
| 1:1 Addition product | 19.90 | 17.40 |
| 1:2 Addition product | 37.70 | 39.40 |
| 1:3 Addition product | 3.60 | 4.20 |

EXAMPLE 2

The reagents are as follows:
$NiCl_2(PMe_3)_2$ 0.35 mmol
EADC 10.5 mmol
   methyl ester (65% of C18:2)
   58.0 mmol (of C18:2 conj)
   or 30 ml of ester The operating conditions are as follows:
T=80° C.; ethylene pressure=3 MPa; time=3 hours.

The reducing agent is introduced under a low ethylene pressure into the ester solution at 80° C. that contains the nickel complex. Then, the equipment is put under a pressure of 3 MPa of ethylene while the mixture is stirred with a bar magnet.

After 3 hours of reaction, the results that are expressed in % by weight are as follows:

| | |
|---|---|
| C16:0 = 6.60 | prod 1:1* = 4.30 |
| C18:0 = 4.40 | prod 1:2* = 22.3 |
| C18:1 = 21.0 | prod 1:3* = 42.0 |

*addition products of 1*, 2* or 3* ethylenes

EXAMPLE 3

At ethylene atmospheric pressure, a complex such as:

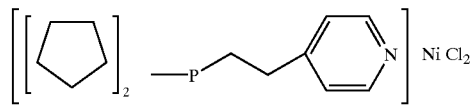

is used with a reducing agent such as EADC. After 3 hours of reaction, on the order of 12% by weight of addition product or 23% of conversion relative to the conjugated linoleate that is present in the mixture of methyl esters of the sunflowerseed oil is formed.

EXAMPLE 4

Other ligands have been used such as trimethylphosphite and triphenyl phosphite.

By using the quantities of reagents below:
Ni(acetylacetonate)$_2$=0.05 mmol, ligand=0.1 mmol,
conjugated ester=5 ml, reducing agent (EADC)=0.3 ml,
the following results are obtained after 3 hours of catalysis at 80° C. under 3 MPa of ethylene pressure:
   with P(OCH$_3$)$_3$, 35% of conversion of 1:1 addition product is reached
   and with P(O-phenyl)$_3$, on the order of 13% of conversion relative to the conjugated methyl linoleate that is present in the ester is reached.

EXAMPLE 5

Instead of ethylaluminum dichloride, it is possible to use isobutylaluminum dichloride.

The reagents are as follows:
- 0.5 mmol of $NiCl_2(PBu_3)_2$ or $NiCl_2[P(cyclohexyl)_3]_2$ or $NiCl_2[P(isopropyl)_3]_2$
- 5 mmol of isobutylaluminum dichloride
- 50 ml of sunflowerseed methyl ester that contains 65% conjugated methyl linoleate.

The operating conditions are as follows:
Temperature=80° C.; P=3 MPa; time=3 hours.

The results that are obtained are as follows:

| Complexes | Time | C16:0 | C18:0 | C18: 1 + 2 | 1:1 Prod | 1:2 Prod | 1:3 Prod |
|---|---|---|---|---|---|---|---|
| $NiCl_2(P\text{-}Bu_3)_2$ | 4 h | 7.0 | 5.3 | 24.5 | 13.5 | 16.9 | 32.8 |
| $NiCl_2(P\text{-}Cycl_3)_2$ | 4 h | 6.9 | 4.8 | 71.5 | 16.8 | — | — |
| $NiCl_2(P\text{-}IsPr_3)_2$ | 5 h | 6.6 | 4.7 | 71.7 | 17.0 | — | — |

EXAMPLE 6

It is also possible to use a less acidic reducing agent such as diethylaluminum chloride (DEAC). A 1:1 addition product conversion on the order of 23% is obtained with the complex $NiCl_2(PBu_3)_2$ and for an Ni/DEAC stoichiometry=1:15 at a temperature of 80° C., under a pressure of 3 MPa and with 60 ml of conjugated sunflowerseed methyl ester.

EXAMPLE 7

It is also possible to use an already reduced complex, then to add a reducing agent.

When a ligand is not added, no addition products are formed.

With the following conditions:
temperature=80° C., P=3 MPa
and by using the following reagents:
- $Ni(COD)_2$ 0.35 mmol (COD=cyclooctadiene)
- EADC 10.5 mmol molar ratio=1/30
- conjugated ester 30 ml no conversion is obtained after 3 hours of reaction.

EXAMPLE 8

The same conditions as in Example 7 are reproduced, but by introducing in addition one mol of triphenylphosphine relative to nickel. In this case, a reaction product is obtained whose composition, expressed in % by weight, is as follows:

| | |
|---|---|
| C16:0 | 6.0 |
| C18:0 | 4.2 |
| C18:1 | 20.3 |
| C18:2 | 16 |
| C18:2 conj | 24.4 |
| 1:1 add prod | 32.8 |
| 1:2 add prod | 10.5 |
| 1:3 add prod | traces |

The yield that is expressed in % by weight, obtained relative to the conjugated methyl linoleate, is on the order of 63%.

EXAMPLE 9

It is also possible to use a conjugated ethyl ester that is easily produced from a sunflowerseed oil ethyl ester or else by esterification of conjugated fatty acids.

The reagents are as follows:
- $NiCl_2(PBu_3)_2$ 10 g or 0.019 mol
- EADC 24 ml or 0.232 mol (Ni/red=1:12)
- conjugated ethyl ester 1500 ml (the acidity of this ester is less than 1 mmol/100 g).

The test conditions are as follows:
Temperature=80° C.; P=0.1 MPa; Catalysis time=8 hours.

As a function of catalysis time, the following results are obtained:

| Time Products | 1 hour | 3 hours | 6 hours | 8 hours |
|---|---|---|---|---|
| C16:0 | 3.4 | 3.6 | 3.5 | 3.5 |
| C18:0 | 1.5 | 1.5 | 1.5 | 1.4 |
| C18:1 | 25 | 27.2 | 26.2 | 25.8 |
| C18:2 | 4.2 | 3.3 | 3.8 | 2.9 |
| C18:2 conj | 39.2 | 32.4 | 0 | 0 |
| 1:1 add prod | 21.3 | 13.9 | 10.1 | 9.0 |
| 1:2 add prod | 4.8 | 14.1 | 48.3 | 47.7 |
| 1:3 add prod | 0.6 | 4.0 | 6.6 | 9.7 |
| conversion (%) | 38 | 49 | 100 | 100 |

It is noted that heavier esters are formed with the addition of 2 mol of ethylene even before the conjugated ester is exhausted.

Consequently, it is possible to imagine that the catalyst is very conjugating or isomerizing, which, for that matter, is visible in the CPG chromatogram with the appearance of new peaks of C18:1.

EXAMPLE 10

It is not necessary to start from a conjugated ester.

With the nickel complex; $NiCl_2(PBu_3)_2$ and a molar ratio of Ni/EADC that is equal to 1:20, the following results are obtained at an ethylene pressure of 0.1 MPa and in the presence of sunflowerseed methyl ester that contains 61.6% of unconjugated methyl linoleate:

| Products After | 2 Hours | 4 Hours |
|---|---|---|
| C18:2 | 37.4% | 27.6% |
| C18:2 conj | 1.6% | ND* |
| 1:1 addition products | 8.7% | |
| 1:2 addition products | 5.7% | 36.2% |
| 1:3 addition products | 8.3% | isomer mixture |

*ND: has not been determined

EXAMPLE 11

It is possible to produce trimethylolpropane triethylstearate (TMP) by reacting methyl ethyl-stearate with TMP.

The physical properties that are obtained are compared with different TMP esters that are obtained from branched, unbranched, saturated or polyunsaturated fatty acids.

| Products Tests | Methyl ethyl-stearate | Tri-ethyl-stearate of TMP* | Tri-iso-stearate of TMP* | Tri-ethyl-linoleate of TMP | Tri-lino-leate of TMP |
|---|---|---|---|---|---|
| Cloud point | −11° C. | −35° C. | −33° C. | −12° C. | −6° C. |
| Pour point | −33° C. | <−53° C. | −33° C. | −51° C. | −12° C. |

-continued

| Products Tests | Methyl ethyl- stearate | Tri- ethyl- stearate of TMP* | Tri-iso- stearate of TMP* | Tri- ethyl- linoleate of TMP | Tri- lino- leate of TMP |
|---|---|---|---|---|---|
| Viscosity in mm²/s at 40° C. | 6.8 | 92.7 | 103 | 67 | 34 |
| Viscosity in mm²/s at 100° C. | 2.2 | 14 | 13.5 | 12 | 7.5 |
| Viscosity index | 140 | 155 | 130 | 177 | 19.4 |
| Thermal stability** | 205° C. | 340° C. | 290° C. | 330° C. | 280° C. |

*Product produced from commercial isostearic acid.
**Produced under argon atmosphere by thermogravimetry.

It is noted the tri-ethyl stearate of TMP (product purified by hydrogenation and crystallization) has much more advantageous properties than the non-purified product (tri-ethyl linoleate of TMP). In addition, maintaining unsaturation of the fatty chain is a handicap for stability with oxidation of the molecule.

EXAMPLE 12

The sodium salts and the monoglycerides of branched acids have very low interfacial tensions relative to water and to gas oil.

The results are recorded in the table below.

| Products | CMC¹ (g/l) | Interfacial Tension (mN/m) |
|---|---|---|
| 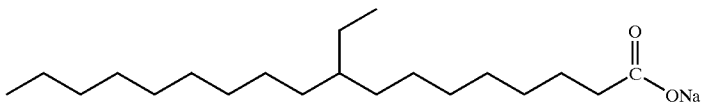  Soap of isoarachidic acid C20 | 0.01 | 5.27 |
| 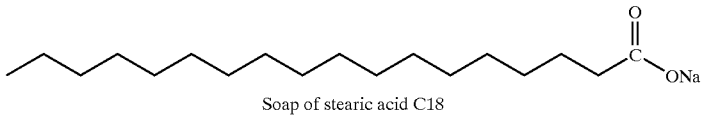  Soap of stearic acid C18 | 0.1–0.2 | 7.16 |
| 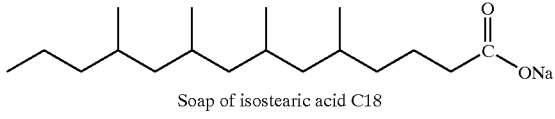  Soap of isostearic acid C18 | 0.05–0.1 | 0.15 |
| 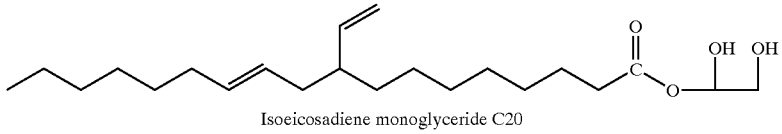  Isoeicosadiene monoglyceride C20 | 0.005 | too weak |

*Critical micellar concentration

Several milligrams of monoglyceride of the branched acid can almost completely reduce the interfacial tension between the water and the gas oil.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for producing a fatty substance comprising a fatty linear hydrocarbon chain, and along said chain at least one hydrocarbon branch of at least two carbon atoms, said process comprising reacting by addition at least one monoolefinic compound onto a compound having a fatty chain containing at least two conjugated or unconjugated ethylenic bonds, in the presence of a catalytic system comprising:

at least one nickel compound;
a member selected from the group consisting of at least one reducing compound, at least one Bronsted acid, at least one Lewis acid and mixtures thereof; and
at least one ligand.

2. A process according to claim 1, wherein in said catalytic system, the nickel compound is a bivalent, monovalent or zerovalent, inorganic or organic nickel salt;
the reducing compound is an organoaluminum compound, an organomagnesium compound, an aluminum hydride or an aluminoxane;
the ligand is selected from the groups consisting of:
from among the phosphorus compounds of formula $PR_mX_{3-m}$ with m=2 or 3; R=aryl or alkyl; X=halogen; phosphites of formula $P(OR)_3$, with R=aryl or alkyl; phosphine oxides $POR_3$, and diphosphines of formula $R_2P-(CH_2)_n-PR_2$, with R=aryl or alkyl; n=0–4;
from among the compounds of arsenic and antimony analogous to said phosphorus compounds; and from among nitrogenous ligands, amide ligands, imines, diimines and pyridines.

3. A process according to claim 1, wherein said monoolefinic compound is ethylene, propylene, or butene-1.

4. A process according to claim 1, wherein said fatty substance that comprises at least one ester having at least two ethylene bonds, conjugated or can be conjugated, the fatty chain comprises 18 to 26 carbon atoms on the chain that carries a carboxylic group, with the latter being linked to a mono-, di-, tri- or tetrafunctional alcohol with 1 to 22 carbon atoms.

5. A process according to claim 4, wherein the alcohol is methanol, ethanol, neopentylglycol, trimethylolpropane, 2-ethylhexanol, glycerol, or a fatty alcohol of $C_{16}$ to $C_{22}$.

6. A process according to claim 1, wherein the catalytic system comprises, as a nickel compound, a halide, acetylacetonate or carboxylate and, as a reducing agent, a system with an unsubstituted or substituted alkylaluminum base, or an aluminoxane or an aluminum hydride, whereby the molar ratio between the nickel and the reducing agent is 1 to 30.

7. A process according to claim 1, wherein said ligand is of the formula $PR_mX_{3-m}$, $P(OR)_3$ or $R_2P-(CH_2)_n-PR_2$, with m=2 or 3, n=1, 2, 3 or 4 X is halogen and R=alkyl or aryl, wherein the molar ratio between the nickel and the ligand is 1 to 10.

8. A process according to claim 1, wherein the fatty substance is an ester present in conjugated form or is conjugated during the reaction of the at least one monoolefinic compound.

9. A process according to claim 7, wherein the catalytic system is obtained by reaction, of a complex Ni(diolefin)$_2$, with a Bronsted or Lewis acid and a phosphine ligand of the formula $POR_3$ or $R_3P-(CH_2)_n-PR_2$ with R being aryl or alkyl and n=0–4.

10. A process according to claim 1, wherein the monoolefinic compound is present in a sufficient quantity to result in at least one branch having a length that is double or triple that of the monoolefinic compound.

11. A process for preparation of a saturated branched compound comprising hydrogenating a branched compound obtained according to claim 1, in the presence of said catalytic system or a different hydrogenation catalyst, optionally after filtration or elimination of said catalytic system.

12. A process according to claim 11, further comprising purifying the saturated branched compound obtained by hydrogenation after the branched compounds are separated by distillation and/or by elimination of the unbranched saturated compounds by crystallization in a solvent.

13. A saturated mono-, di- and/or tri-branched compound obtained by a process according to claim 12.

14. A process according to claim 13 further comprising modifying the carboxylic function to produce an alcohol, amide or amine, whereby the fatty chain maintains the branches.

15. A lubricant composition comprising as a lubricant base, a saturated compound according to claim 13.

16. A process according to claim 6, wherein the molar ratio between the nickel and the reducing agent is 4 to 15.

17. A process according to claim 7, wherein the molar ratio between the nickel and the ligand is 1 to 4.

18. A process according to claim 9, wherein the Bronsted or Lewis acid is a Lewis acid selected from the group consisting of HCl, HAlCl$_4$, HAlF$_4$, HPF$_6$ and HSbF$_6$.

19. A process according to claim 9, wherein said diolefin is cyclooctadiene or norbornadiene.

20. A process according to claim 1, wherein said catalytic system comprises nickel dichloride, tributyl phosphine and ethylaluminum dichloride.

21. A process according to claim 1, wherein said catalytic system comprises nickel dichloride, trimethyl phosphine and ethylaluminum dichloride.

22. A process according to claim 1, wherein said catalytic system comprises nickel dichloride, 1-(4 pyridyl ethyl)2-bis (cyclopentyl)phosphine and ethylaluminum dichloride.

23. A process according to claim 1, wherein said catalytic system comprises nickel bis(actelyacetonate), trimethylphosphite or triphenyl phosphite, and ethylaluminum dichloride.

24. A process according to claim 1, wherein said catalytic system comprises nickel dichloride tributyl phosphine or tricyclohexylphosphine or triisopropylphosphine, and isobutylaluminum dichloride.

25. A process according to claim 1, wherein said catalytic system comprises nickel dichloride tributylphosphine and diethylaluminum chloride.

26. A process according to claim 1, wherein said catalytic system comprises cyclooctadiene nickel, triphenylphosphine and ethylaluminum dichloride.

27. A process according to claim 1, conducted under conditions sufficient to provide a composition containing a mixture comprising:
(A) at least one compound having one ethylene branch added to said fatty chain,
(B) at least one compound having two ethylene branches added to said fatty chain, and
(C) at least one compound having three ethylene branches added to said fatty chain.

28. A process according to claim 27, wherein the catalyst comprises NiCl$_2$ (P—Bu$_3$)$_2$.

29. A composition produced according to claim 27.

30. A composition produced according to claim 28.

31. A process according to claim 18, wherein said diolefin is cyclooctadiene or norbornadiene.

32. A process according to claim 24, wherein the catalytic system comprises nickel dichloride tributyl phosphine.

33. A process according to claim 27, wherein the fatty chain has two ethylenic bonds.

34. A process according to claim 33, wherein the catalyst comprises NiCl$_2$ (P—Bu$_3$)$_2$.

35. A composition produced according to claim 33.

36. A composition produced according to claim 34.

37. A composition according to claim 29, wherein the ethylenic bonds are thereafter hydrogenated so as to yield a saturated composition.

38. A composition according to claim 35, wherein the ethylenic bonds are thereafter hydrogenated so as to yield a saturated composition.

39. A process according to claim 1, wherein the catalytic system comprises at least one reducing compound of the formula AlX$_2$R wherein X represents halogen and R represents alkyl.

* * * * *